(12) United States Patent
Rigneault et al.

(10) Patent No.: US 9,097,674 B2
(45) Date of Patent: Aug. 4, 2015

(54) METHOD FOR DETECTING A RESONANT NONLINEAR OPTICAL SIGNAL AND DEVICE FOR IMPLEMENTING SAID METHOD

(75) Inventors: Hervé Rigneault, Allauch (FR); David Gachet, Beaumont-les-Valence (FR); Sophie Brustlein, Marseilles (FR); Franck Billard, Dijon (FR)

(73) Assignee: Centre National de la Recherche Scientifique—CNRS, Paris (FR)

( * ) Notice: Subject to any disclaimer, the term of this patent is extended or adjusted under 35 U.S.C. 154(b) by 367 days.

(21) Appl. No.: 13/574,508

(22) PCT Filed: Jan. 18, 2011

(86) PCT No.: PCT/EP2011/050619
§ 371 (c)(1),
(2), (4) Date: Sep. 12, 2012

(87) PCT Pub. No.: WO2011/089118
PCT Pub. Date: Jul. 28, 2011

(65) Prior Publication Data
US 2013/0038871 A1 Feb. 14, 2013

(30) Foreign Application Priority Data
Jan. 22, 2010 (FR) .................................. 10 00245

(51) Int. Cl.
*G01J 3/44* (2006.01)
*G01N 21/65* (2006.01)

(52) U.S. Cl.
CPC . *G01N 21/65* (2013.01); *G01J 3/44* (2013.01); *G01J 3/4412* (2013.01); *G01N 21/658* (2013.01); *G01N 2021/653* (2013.01); *G01N 2021/655* (2013.01)

(58) Field of Classification Search
CPC .......... G01J 3/44; G01J 3/4412; G01N 21/65; G01N 21/658
USPC .......................................................... 356/301
See application file for complete search history.

(56) References Cited

U.S. PATENT DOCUMENTS 5,929,981 A * 7/1999 Keilbach ......................... 356/73
6,169,289 B1 1/2001 White et al.
(Continued)

FOREIGN PATENT DOCUMENTS

DE WO2009149733 * 12/2009 ......... G01N 15/1459
GB 1171689 A 11/1969

OTHER PUBLICATIONS

International Search Report and Written Opinion of the International Searching Authority for International Application No. PCT/EP2011/050619 mailed in May 17, 2011, with English translation thereof (22 pages).
(Continued)

*Primary Examiner* — Tarifur Chowdhury
*Assistant Examiner* — Sunghee Y Gray
(74) *Attorney, Agent, or Firm* — Osha Liang LLP

(57) ABSTRACT

A method and a device for detecting a resonant non-linear optical signal induced in a sample including a resonant medium and a non-resonant medium forming an interface is disclosed. The device includes an excitation light beam that intercepts the sample along an optical axis. The device further includes a first optical detection module for detecting a non-linear optical signal resulting from the interaction of the beam with the sample, and a mirror that reflects the excitation beam. The device further includes a second optical detection module for detecting a nonlinear optical signal resulting from the interaction of the reflected excitation beam with the sample, and a processing module for processing the optical signals, detected by the first and second detection modules. Processing the optical signals includes calculating a difference in the detected signals, the difference being characteristic of a vibrational or electronic resonance of the resonant medium.

16 Claims, 11 Drawing Sheets

(56) References Cited

U.S. PATENT DOCUMENTS

| | | |
|---|---|---|
| 6,614,532 B1 | 9/2003 | Power et al. |
| 2002/0105722 A1* | 8/2002 | Bewersdorf et al. ........... 359/370 |
| 2004/0142484 A1* | 7/2004 | Berlin et al. .................. 436/171 |
| 2006/0192969 A1* | 8/2006 | Marks et al. .................. 356/451 |
| 2007/0121119 A1 | 5/2007 | Martinez |
| 2010/0232459 A1* | 9/2010 | Hashimoto et al. ............. 372/25 |
| 2011/0164246 A1* | 7/2011 | Riddell ......................... 356/301 |

OTHER PUBLICATIONS

Gachet et al, "Focused Field Symmetries for Backgound-Free Coherent Anti-Stokes Raman Spectroscopy" The American Physical Review, vol. 77, No. 6, Jun. 2, 2008 (4 pages).

Schie et al, "Simultaneous Forward and Epi-CARS Microscopy with a Single Detectorby Time-Correlated Single Photon Counting," Optics Express, Optical Society of America, vol. 16, No. 3, Feb. 4, 2008 (8 pages).

M. S. Silver et al, "Selective spin inversion in nuclear magnetic resonance and coherent optics through an exact solution of the Bloch-Riccati equation"; vol. 31, No. 4, The American Physical Society, Apr. 1985 (3 pages).

H.-J. Briegel1,2,* et al, "Quantum repeaters for communication"; Institut für Theoretische Physik, Universität Innsbruck, Technikerstrasse 25, A-6020 Innsbruck, Austria; Departmento de Fisica, Universidad de Castilla-La Mancha, 13071 Cuidad Real, Spain, arXiv:quant-ph/9803056v1, Mar. 20, 1998 (8 pages).

N. Sangouard et al., "Analysis of a quantum memory for photons based on controlled reversible inhomogeneous broadening"; Group of applied Physics-Optics, University of Geneva, Switzerland, arXiv:quant-ph0611165v2, Jan. 30, 2007 (9 pages).

V. Damon et al., Revival of silenced echo and quantum memory for light; Laboratoire Aimé Cotton, CNRS-UPR 3321, Univ. Paris-Sud, Bât. 505, 91405 Orsay cedex, France, New Journal of Physics 13, Sep. 20, 2011 (13 pages) (http://iopscience.iop.org/1367-2630/13/9/093031).

* cited by examiner

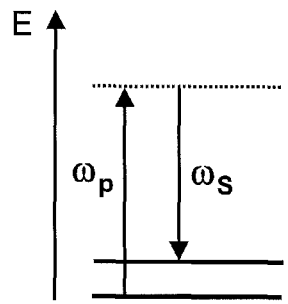
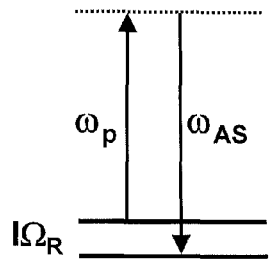
FIG.1A  FIG.1B
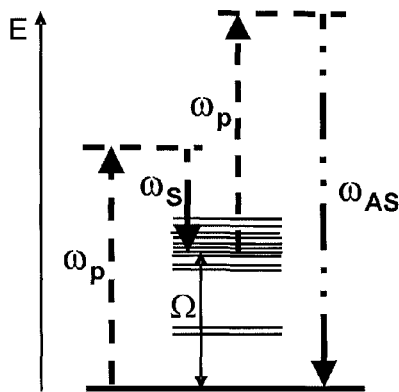
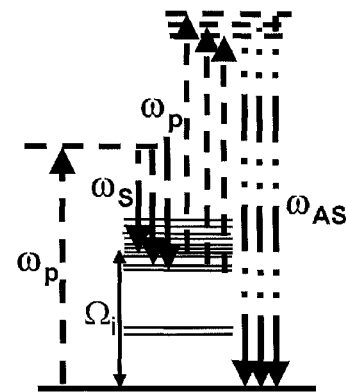
FIG.2A  FIG.2B
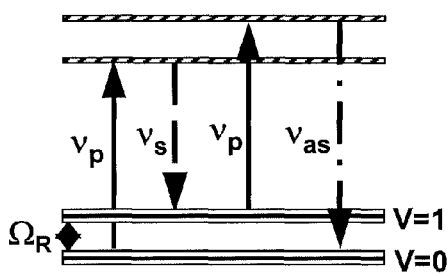
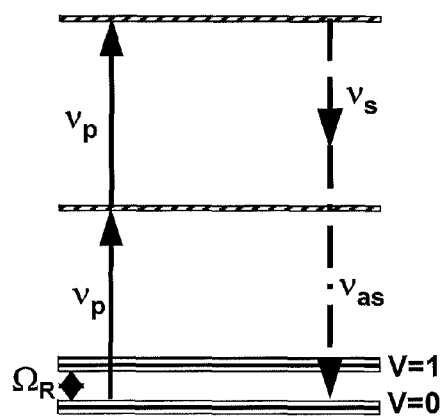
FIG.3A  FIG.3B

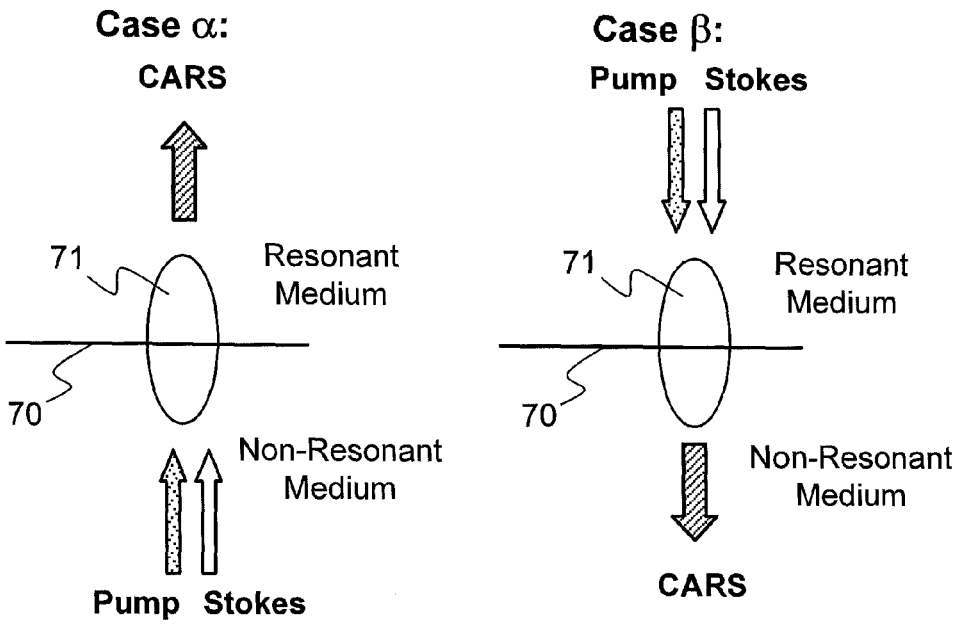
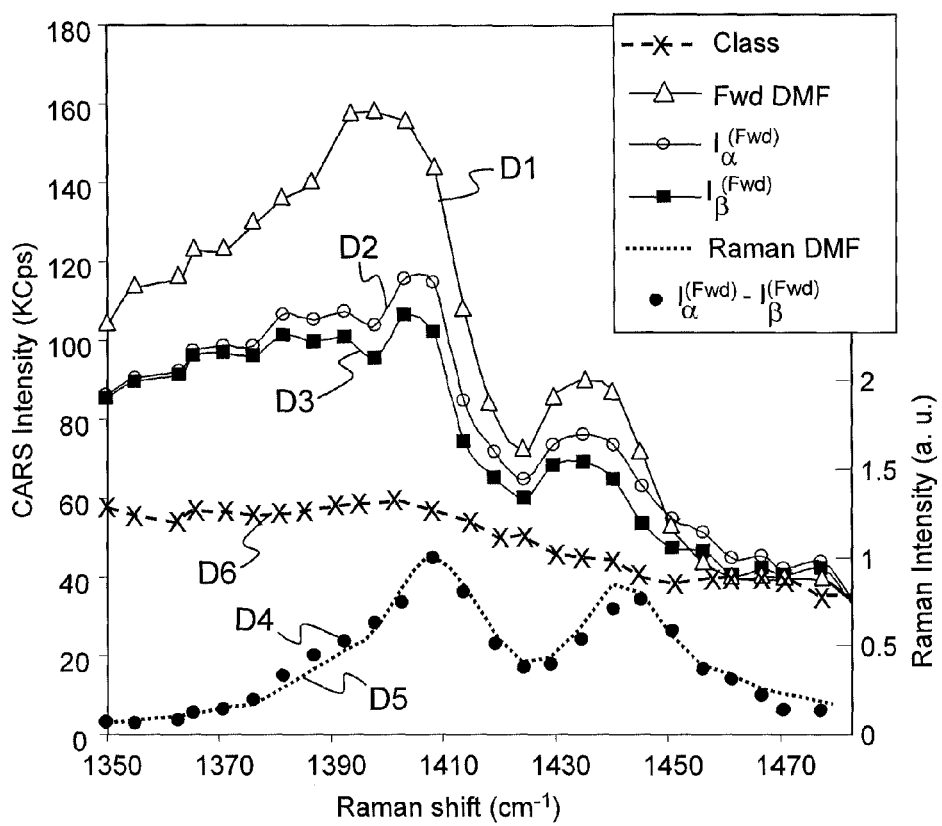
FIG.9

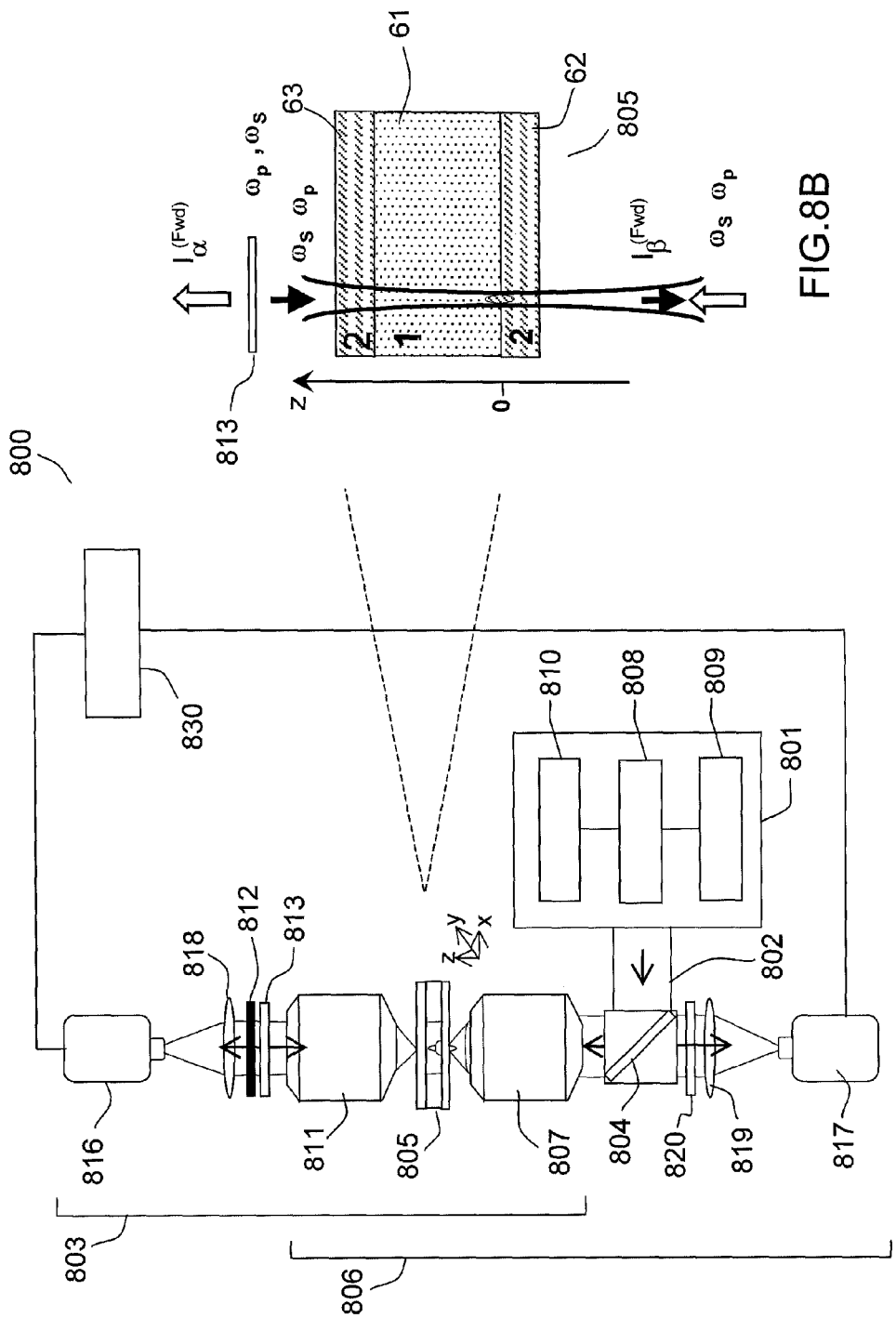

METHOD FOR DETECTING A RESONANT NONLINEAR OPTICAL SIGNAL AND DEVICE FOR IMPLEMENTING SAID METHOD

PRIOR ART

1. Technical Field of the Invention

The present invention relates to a method for detecting a resonant nonlinear optical signal and a device for implementing said method. It is particularly applicable to the detection of CARS scattered signals.

2. Prior Art

All chemical bonds have their own characteristic vibration frequency. Methods aimed at using the light/matter interaction to obtain information on these molecular vibrations are called vibrationally-sensitive optical techniques. The most well-known of these techniques is infrared (IR) spectroscopy, which observes the absorption lines specific to chemical bonds present in a sample. Discovered in 1928, Raman scattering (from the name of a physicist, Chandrasekhara Venkata Raman, who discovered the effect) allows visible light to be used to access the vibrational spectrum of molecules which interact with a light beam. In Raman scattering, a pump wave of angular frequency $\omega_P$ incident on a molecule is scattered inelastically into a wave called a Stokes wave, of angular frequency $\omega_S$ (FIG. 1A) and a wave called an anti-Stokes wave, of angular frequency $\omega_{AS}$ (FIG. 1B). The difference in frequency between the generated waves and the pump wave depends on the molecular Raman transition (of angular frequency $\Omega_R$) such that $\omega_p - \omega_s = \omega_{as} - \omega_p = \Omega_R$. In a photonic view of the process, the Stokes and anti-Stokes waves correspond to absorption from the fundamental or excited vibrational level respectively. The process generating the anti-Stokes wave, from the excited vibrational level (B), is much less probable than the process creating the Stokes wave, which is the only one observed in practice in spontaneous Raman spectroscopy. Detailed study of the spectral distribution of Stokes waves yields information about the densities of chemical bonds present in the sample. This spontaneous process of inelastic scattering is very inefficient compared with fluorescence (Raman cross-sections are of the order of $10^{-+}$ cm$^2$/molecule, compared with the absorption cross-section of 1 photon of a fluorophore, which reaches $10^{-16}$ cm$^2$/molecule).

Stimulated CARS (Coherent Anti-Stokes Raman Scattering) Raman spectroscopy is a four-wave mixing process that allows the vibrational bonds present in a sample to be addressed. This process is described, for example, in R. W. Boyd, *Nonlinear Optics* (Academic Press, Boston, 1992). It involves sending two laser pulses of angular frequencies $\omega_p$ and $\omega_s$ (or of frequencies $v_p$ and $v_s$), the angular frequency difference of which is equal to the angular frequency $\Omega$ at the vibrational level under investigation. In this resonance configuration $\omega_p - \omega_s = \Omega$, the vibrational level of angular frequency $\Omega$ is populated in a stimulated manner and will be able to scatter inelastically the beam of angular frequency $\omega_p$ into a beam of angular frequency $\omega_{as} = 2\omega_p - \Omega_s$ (FIG. 2A). The presence of this new radiation $\omega_{as}$ is the signature of the presence of the bond vibrating at the angular frequency $\Omega$ in the sample. A first implementation of CARS consists directing at the sample two pulses which are spectrally picosecond narrow, the angular frequency difference of which addresses only one specific vibrational bond. For optimum identification, all the vibrational bonds present in the sample are tested. This is done by operating in a mode called "Multiplex CARS" (see, for example, M. Muller and J. Schins, "Imaging the thermodynamic state of lipidic membranes with multiplex CARS spectroscopy", Physical Chemistry B 106, 3715-3723 (2002)) where a spectrally narrow pulse $\omega_p$ and a spectrally wide pulse $\omega_s$ are directed at the sample (FIG. 2B). Thus all the vibrational levels $\Omega_i$ present in the sample can be addressed, and a spectrum of the generated signal $\omega_{as}$ can be obtained. From a technical point of view, the narrow spectrum originates, for example, from a picosecond laser and the wide spectrum, for example, from a femtosecond laser, or a photonic crystal fibre generating a supercontinuum (SC).

In FIG. 3A the process of resonant CARS scattering is described, which is used to access the signature of the molecular to be identified. However, a non-resonant CARS contribution exists, represented in FIG. 3B, which arises from an electronic contribution of the sample. This non-resonant contribution may be important when CARS spectroscopy is performed on a sample comprising a wide diversity of chemical bonds.

In the article "Focused field symmetries for background-free coherent anti-Stokes Raman spectroscopy", Physical Review A 77 (2008), in the name of D. Gachet et al., an original method is presented which allows the non-resonant contribution to be eliminated. FIGS. 4 to 6 illustrate the method. This consists in producing a differential CARS image between an object and its mirror image about a transverse interface 43 between a resonant medium (reference numeral 41 in FIGS. 4A and 4B) and a non-resonant medium (reference numeral 42 in FIGS. 4A and 4B). The 3rd order nonlinear susceptibility is defined in the resonant medium 41 by a resonant term $\chi^{(3)}_{1R}$ and a non-resonant term $\chi^{(3)}_{1NR}$. In the non-resonant medium 42, it is defined by the non-resonant term $\chi^{(3)}_{2NR}$. FIGS. 4A and 4B depict an active CARS volume 45 (focal point of pump and Stokes beams of frequencies $\omega_p$ and $\omega_s$ respectively), located on the transverse interface 43 between the resonant medium and the non-resonant medium. Two situations are envisaged: case $\alpha$ wherein the pump and Stokes beams are incident on the non-resonant medium side, and case $\beta$ wherein the pump and Stokes beams are incident on the resonant medium side. It is demonstrated in this article that the difference between the CARS signals obtained in cases $\alpha$ and $\beta$ comprises only the resonant contribution of the resonant medium. FIG. 5 illustrates the results of a numerical calculation taking into account the vectorial nature of the pump and Stokes beams focused on a transverse interface as illustrated in FIGS. 4A and 4B. The analysis consists in studying the difference $\Delta I_{Fwd}$ of the CARS signals emitted in problems $\alpha$ ($I_\alpha$(Fwd)) and $\beta$ ($I_\beta$(Fwd)) as a function of the normalised Raman shift $\zeta = (\omega_p - \omega_s - \Omega_R)\Gamma$ (where $\Gamma$ is the spectral width of the vibrational line studied). It is demonstrated that the difference $\Delta I_{Fwd}$ exactly follows the imaginary part of $\chi^{(3)}_{1R}$ which is known to be the Raman spectrum of medium 1. An experimental implementation of the method is illustrated in FIG. 6B and the experimental results are presented in FIG. 6A. FIG. 6B represents a sample composed of a layer 61 of DMF (N,N-dimethylformamide) between two glass slides 62, 63. Case $\alpha$ corresponds to the case wherein the pump and Stokes beams are focused on the glass-DMF interface (interface between 62 and 61), while case $\beta$ corresponds to the case wherein the excitation beams are focused on the DMF-glass interface (interface between 61 and 63). In FIG. 6A, as a function of the Raman shift respectively, curve C1 illustrates the CAR intensity of the DMF alone (when the excitation beams are focused in the resonant medium); curve C2, the intensity $I_\alpha$(Fwd); curve C3, the intensity $I_\beta$(Fwd); curve C4, the differential $\Delta I_{Fwd}$, and curve C5 the Raman spectrum. It appears, as demonstrated theoretically, that the method enables elimination of the non-resonant component which soils the CARS scattered signal represented by curve C1.

However, this method has a number of drawbacks. Notably, it is limited to symmetric samples, such as shown in FIG. 6B, or reversible ones, in order to have access to resonant/non-resonant interfaces on the one hand and non-resonant/resonant interfaces on the other. This has a limitation in the cases of biological samples which rarely have these properties. Furthermore, although it allows spectroscopy applications, this method is limited for microscopy applications.

The present invention proposes a novel device for detecting a resonant nonlinear optical signal, based on the principle of transverse interfaces detection as described in the prior art, but which may be applied to any sample having an interface between a resonant medium and a non-resonant medium, both for spectroscopy and microscopy applications.

SUMMARY OF THE INVENTION

According to a first aspect, the invention relates to a device for detecting a resonant nonlinear optical signal induced in a sample of the type comprising a resonant medium and a non-resonant medium forming an interface, the device comprising: an emission source of at least one first excitation light beam, called a pump beam, at a first given angular frequency ωp for the excitation of the resonant medium of a sample of the given type, a first optical module for detecting the nonlinear optical signal resulting from interaction of said incident pump beam the sample when said pump beam is incident on the sample along an optical axis and intercepts the sample at a given position of a transverse interface between the resonant and non-resonant media of the sample, means of reflection of said pump beam, arranged in such a way that said reflected pump beam intercepts said transverse interface substantially at the same position as said incident pump beam, a second optical module for detecting the nonlinear optical signal resulting from interaction of said reflected pump beam with the sample, an optical signal processing module detected by said first and second detection modules, comprising the calculation of a difference in the detected signals, the difference being characteristic of a vibrational or electronic resonance of the resonant medium.

According to a variant embodiment, the emission source allows the emission of a pump beam of angular frequency ωp and a Stokes beam of angular frequency ωs, the nonlinear optical signal resulting from the interaction of said pump and Stokes beams is a signal called a CARS scattered signal, of angular frequency ωas=2ωp−ωs and the difference in signals detected by the first and second detection module is characteristic of a Raman resonance of the resonant medium.

According to another variant embodiment, the device according to the invention comprises a lens for focusing incident excitation beams in a common focal volume, allowing said interface between the resonant medium and the non-resonant medium to be intercepted and a lens for collecting the nonlinear signal resulting from interaction of the incident excitation beams with the sample, said collecting lens being identical to the focusing lens for focusing the incident beams and the collecting lens forming a lens for focusing the reflected excitation beams and the lens for focusing the incident beams forming a lens for collecting the nonlinear signal resulting from interaction of the reflected excitation beams with the sample.

According to another variant embodiment, each of the optical detection modules comprises an image recording device, the nonlinear optical signal being collected in each of the optical detection modules respectively in the symmetrical directions about the optical axis, the difference being effected for each signal couple thus detected.

According to another variant embodiment, a device for angular scanning of the excitation beams allows the excitation beams to intercept the sample at different positions of the interface between the resonant and non-resonant medium.

According to another variant embodiment, the emission source emits at least one variable wavelength excitation beam, allowing a spectrum of vibrational or electronic resonances of the resonant medium to be obtained.

According to a second aspect, the invention relates to a method for detecting a resonant nonlinear optical signal induced in a sample, the sample comprising a resonant medium and a non-resonant medium forming an interface, the method comprising: the emission of at least one first light beam for the excitation of the resonant medium, called a pump beam, at a first given angular frequency ωp, said pump beam being incident on the sample along an optical axis, and intercepting the sample at a given position of a transverse interface between the resonant and non-resonant medium, the detection of a first nonlinear optical signal resulting from interaction of said beam or beams with the sample, the reflection of said excitation beam or beams, the reflected excitation beam or beams intercepting said transverse interface substantially at the same position as the incident excitation beam or beams, the detection of a second nonlinear optical signal resulting from interaction of said reflected excitation beam or beams with the sample, the processing of the first and second detected optical signals, comprising the calculation of a difference in the detected signals, the difference being characteristic of a vibrational or electronic resonance of the resonant medium.

According to a variant embodiment, the method comprises the emission of a pump beam of angular frequency ωp and of a Stokes beam of angular frequency ωs, the nonlinear optical signal resulting from the interaction of said pump and Stokes beams being a signal called a CARS scattered signal, of angular frequency ωas=2ωp−ωs and the difference in the first and second detected signals being characteristic of a Raman resonance of the resonant medium.

According to another variant embodiment, the first and second nonlinear optical signals are detected respectively in symmetrical directions about the optical axis of the incident excitation beams, the difference being effected for each signal couple thus detected.

According to another embodiment, the excitation beam or beams are subject to an angular scan to intercept the sample at various positions of the interface between the resonant and non-resonant medium.

According to another variant embodiment, at least one of the excitation beams has a variable emission wavelength, allowing a spectrum of vibrational or electronic resonances of the resonant medium to be obtained.

BRIEF DESCRIPTION OF THE DRAWINGS

Other advantages and characteristics of the invention will become apparent from reading the description, illustrated by the following FIGS.:

FIGS. 1A and 1B (previously described), principle of Stokes and anti-Stokes emission in a Raman scattering process;

FIGS. 2A and 2B (previously described), principle of CARS emission in two different modes;

FIGS. 3A and 3B (previously described), illustrations of the resonant and non-resonant CARS process;

FIGS. 7A, 7B, illustrations of cases α and β for implementation of the method according to the invention;

FIGS. 8A, 8B, example of the experimental setup for implementation of the method according to the invention;

FIG. 9, experimental results obtained with a sample of the type of that in FIG. 8B;

DETAILED DESCRIPTION

Figure 4A:
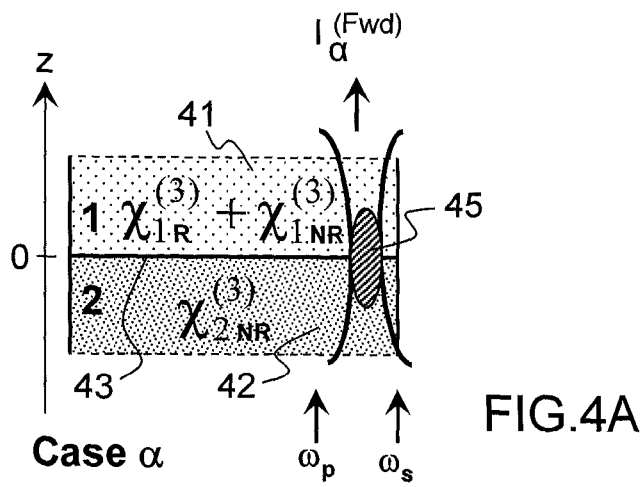
FIGS. 4A and 4B (previously described), illustrations of cases α and β for implementation of the method according to the prior art.
Figure 4B:
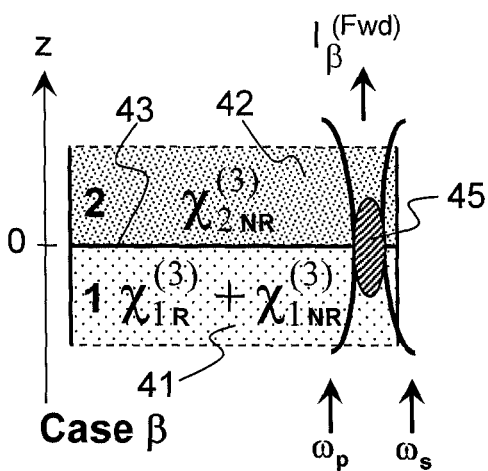
Figure 5:
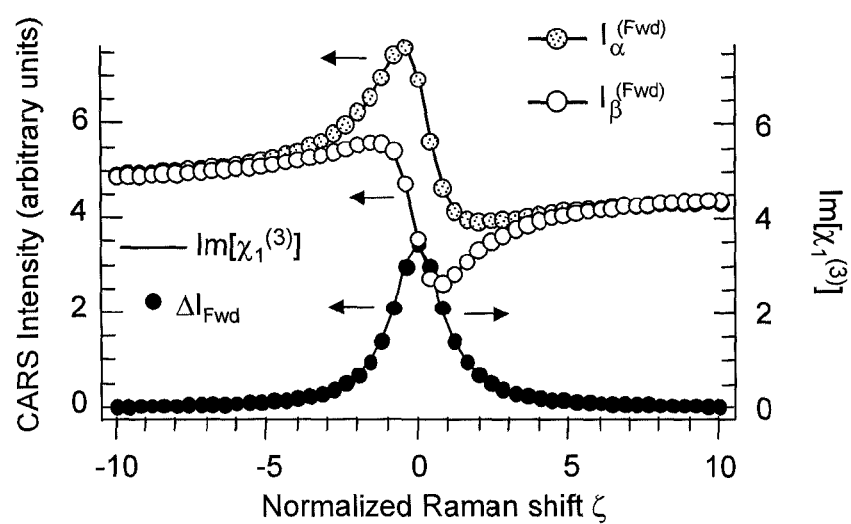
FIG. 5 (previously described), numerical simulations of the results obtained with the method according to the prior art.

FIGS. 7A and 7B illustrate in two diagrams the principle of the detection method according to the invention in the case of CARS scattering. According to the method, a pump beam of angular frequency $\omega_p$ and a Stokes beam of angular frequency $\omega_s$, which are collinear, intercept a transverse interface 70, that is, an interface having a non-zero component along a plane perpendicular to the axes of the incident beams (optical axis), between a non-resonant medium and a resonant medium. In general, the two beams are focused, 71 designating the common focal volume which intercepts the transverse interface 70. According to the invention, the excitation beams cross the interface in a first direction, called case α, and are then reflected towards the sample in such a way as to intercept the same interface at substantially the same position, but in the opposite direction (case β). In the example of FIG. 7, the excitation beams first cross the interface in the direction non-resonant medium/resonant medium (FIG. 7A, case α), then in the direction resonant medium/non-resonant medium (FIG. 7B, case β). The CARS scattered signal intensities $I_\alpha$(Fwd) and $I_\beta$(Fwd) are measured respectively in the two cases α and β, and their difference $\Delta I_{Fwd}$ is calculated, after calibration, to give a signal, which the Applicant has demonstrated is proportional to the imaginary part $Im[\chi^{(3)}_{1R}]$ of the 3rd order nonlinear susceptibility of the resonant medium. According to the invention, a single pulse of the pump beam and Stokes beam is used to excite the sample in cases α and β, allowing the signal-to-noise ratio to be increased as compared with the method according to prior art described in FIGS. 4 to 6.

Taking the difference of the CARS signals generated by an object and its mirror image about a plane perpendicular to the optical axis, the method according to the invention is called Dz-CARS in the following description (Dz standing for Differential imaging in Z symmetry).

FIG. 8A illustrates an example device for implementing the detection method according to the invention. The detection device 800 generally comprises a laser system 801 permitting emission of a first excitation beam of angular frequency $\omega_p$ (pump beam) and of a second excitation beam of angular frequency $\omega_s$ (Stokes beam), which are collinear, the two excitation beams being symbolised by the arrow 802. The device 800 also comprises an optical element, for example reflective sheeting 804, allowing the two excitation beams to be directed into a first optical detection module of the device, generally assigned the reference numeral 803, according to a main direction Z.

The laser system 801 comprises, for example, in a so-called bi-colour application, two spectrally narrow, tunable laser sources 808, for example of the Ti:Sapphire type, emitting at wavelengths between 690 and 1000 nm, pumped by a pump laser 809, Nd:YVO4 type emitting at 532 nm. The tuneable lasers emit, for example, picosecond pulses, typically of the order of 3 ps, to form a pump excitation beam of angular frequency $\omega_p$ (of typical wavelength 730 nm) and Stokes excitation beam of angular frequency $\omega_s$. A pulse picker 810 may be used to reduce the pulse repetition frequency of the pump and probe excitation lasers without reducing the peak pulse power. Using a tuneable Stokes beam or pump beam enables, in particular, the anti-Stokes emission spectrum to be scanned for applications in spectroscopy aimed at determining the Raman spectrum of the resonant medium. Other tuneable laser sources may be used, for example, optical parametric oscillators (OPO), optical parametric amplifiers (OPA), picosecond Nd:glass oscillators, ytterbium or erbium-doped optical fibres, etc. The sources may also be nanosecond or femtosecond laser sources, depending on the spectral width of Raman lines to be observed. However, nanosecond pulses, although very good spectrally, have a lower peak power than ps pulses. Moreover, the thermal effects associated with ns pulses are more capable of damaging biological samples. Raw femtosecond pulses are generally too wide spectrally. In condensed phase (solid or liquid), the line widths are around 10-20 cm$^{-1}$, corresponding to the use of ps pulses.

In the example in FIG. 8A, the first optical detection module 803 comprises a focusing lens 807 intended for focusing the pump and Stokes beams in a common focal volume for analysis of the sample 805 represented in FIG. 8B. Using a focusing lens is particularly appropriate in microscopy applications. However, it is not essential for the emission of the CARS signal to work using focused beams, in particular when studying thin samples. In this example, the sample is formed, as in the example of FIG. 6B, of a layer 61 of DMF (N,N-dimethylformamide) between two glass slides 62, 63. The first optical detection module 803 similarly comprises a collecting lens 811 allowing the emitted nonlinear optical signal to be collected, in this example the CARS scattered signal, and a detector 816, for example a point detector of the avalanche photodiode (APD), rapid photodiode (PIN), or photomultiplier (PMT) type, preceded by a collecting lens 818 and a filter 812 to cut the residual excitation beams.

In this example, the transition from problem α to problem β for a given sample is made by returning the pump and Stokes beams as indicated in FIG. 8A by means of a mirror 813, the coefficient of reflection of which is appropriate for the wavelengths of the excitation beams on the one hand and of the CARS scattered signal on the other, in such a way as to reflect the pump and Stokes beams and transmit the CARS scattered signal resulting from the interaction of the excitation beams with the sample. In this situation, during the first passage of the incident pulses, a first CARS signal is projected and collected by the detector 816; this is then it therefore concerns case α and the collected signal is $I_\alpha$(Fwd). The pump and Stokes pulses are then reflected by the mirror to be returned on to the sample, which is then seen to be in case β, in a second optical detection module overall assigned the reference numeral 806 in FIG. 8A. The second optical detection module 806 comprises in common with the first optical detection module, lenses 811 and 807, but lens 811 acts as a focusing lens for the excitation beams returned by the mirror 813 and lens 807 acts as a collecting lens for the nonlinear optical signal resulting from interaction of the reflected excitation beams with the sample 805. The second optical module 806 furthermore comprises a detector 817, for example a point detector of the same type as detector 816, preceded by a collecting lens 819 and a filter 820 to cut the residual excitation beams. The signal collected behind by detector 817 is then $I_\beta$(Fwd). The difference of signals $I_\alpha$(Fwd)–$I_\beta$(Fwd) is operated in real time, which the Applicant has shown to be proportional to the Raman spectrum of the resonant medium, by means of a processing unit labelled 830 in FIG. 8A. The reflective sheeting 804 is advantageously dichroic sheeting, allowing the excitation beams emitted by the laser source 801 to be reflected towards the sample 805 (case α) while transmitting the CARS scattered signal in case β. The focusing 807 and collecting 811 lenses are advantageously identical, enabling a symmetrical set-up in cases α and β. In practice, detectors 816, 817 are calibrated prior to measurement. For example, this calibration is performed on a sample comprising only solvent.

As can be seen in FIG. 8B, the device according to the invention allows the same pump and Stokes pulses to intercept the sample at the same position of the transverse interface, in cases α and β respectively. The method can thus be used with any type of sample presenting an interface between a resonant medium and a non-resonant medium, and not just a symmetrical or reversible sample.

According to one example, the device 800 also comprises an excitation beam scanning device in plane XY of the sample (not shown). This scanning device may be useful at one and the same time in spectroscopy applications, for adjusting the focal point of the excitation beams over a transverse interface of the resonant and non-resonant media forming the sample, that is, in imaging applications. It may act as a device allowing displacement of the sample, or preferably, as an excitation beam scanning device. A spherical excitation beam-reflecting mirror 813 can advantageously be used in such a way as to reflect the excitation beams in an antiparallel direction, which will allow the reflected excitation beams (case β to intercept the sample at the same position as that of the incident beams (case α).

FIG. 9 illustrates the experimental results obtained with the device of FIG. 8A and a sample of the type in FIG. 8B, in which a fine layer of DMF (N,N-dimethylformamide) serves as the resonant medium between two glass slides (here serving as the non-resonant medium). The wavelength of the pump beam is 730 nm, that of the Stokes excitation beam around 814 nm. The numerical aperture in air of lenses 807, 811 is 0.6. In FIG. 9, as a function of the Raman shift respectively, curve D1 illustrates the CARS scattered signal measured in the DMF; curve D2, the intensity $I_\alpha$(Fwd) measured in case α (FIG. 6B); curve D3, the intensity $I_\beta$(Fwd) measured in case β, curve D4, the difference $\Delta I_{Fwd}$, curve D5 (dotted line) the Raman spectrum, and curve D6 the CARS scattered signal measured on the glass. Curve D1 reveals clearly the distortion effect due to the non-resonant contribution of the resonant medium, while the difference $\Delta I_{Fwd}$ is superimposed exactly on the Raman spectrum of DMF (dotted line). Thus one can appreciate the capacity of Dz-CARS to extract the Raman spectrum of the resonant medium without any distortion due to the non-resonant part of the resonant medium.

Figure 6A:
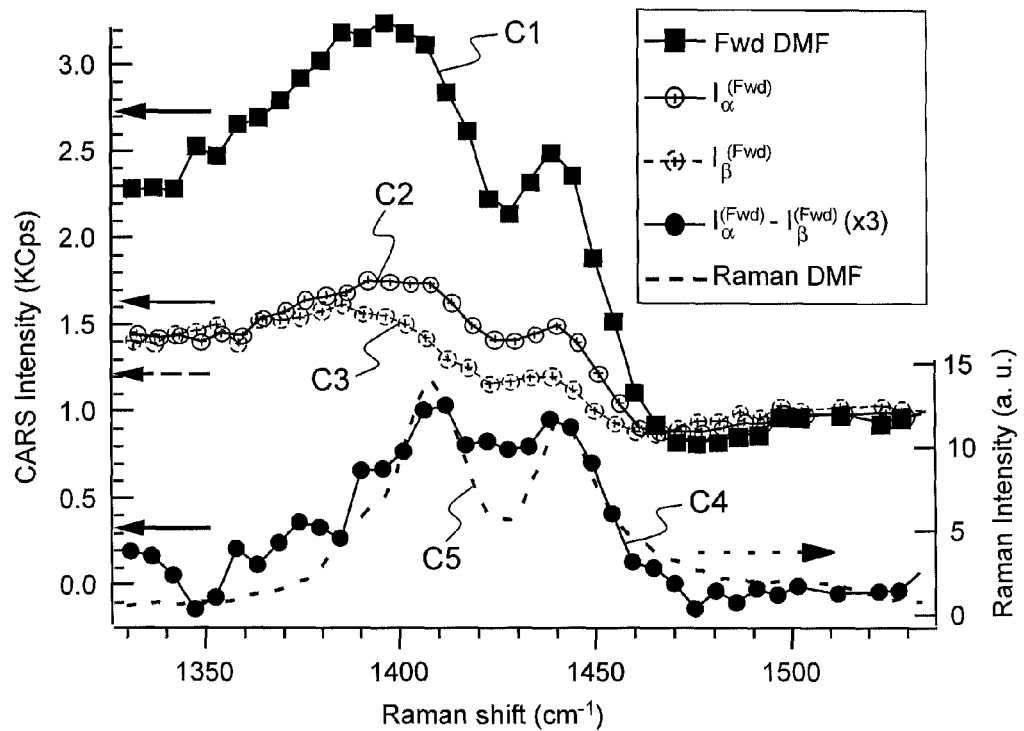
FIGS. 6A and 6B (previously described), experimental results obtained with a symmetrical sample, by the method according to the prior art.
Figure 6B:
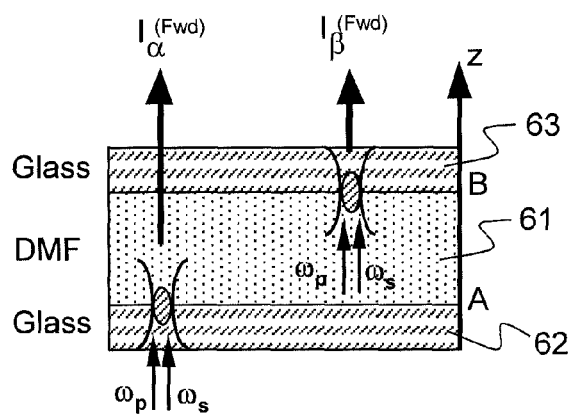

The experimental results demonstrate the relevance of the Dz-CARS approach for noiseless, non-resonant CARS spectroscopy, and with a precision distinctly improved by comparison with the prior art, as illustrated in FIG. 6A. Furthermore, the method according to the invention allows perfect identification of the position on the interface on which one is working, and focusing of identical excitation pulses at the same position of the interface as in cases α and β, notably enabling microscopy applications.

Figure 10A:
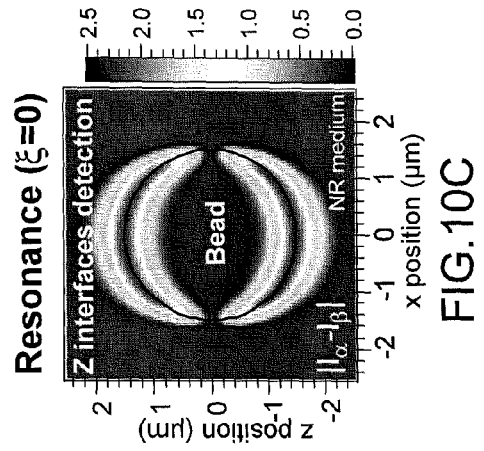
FIGS. 10A to 10D, images obtained by numerical simulation with a polystyrene bead of 3-μm diameter, immersed in an aqueous liquid with a refraction index n=1.33, by the method according to the invention.
Figure 10B:
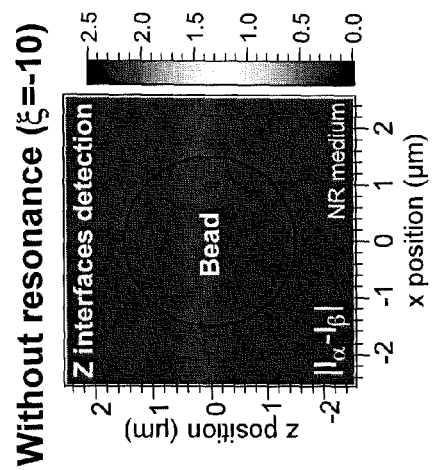
Figure 10C:
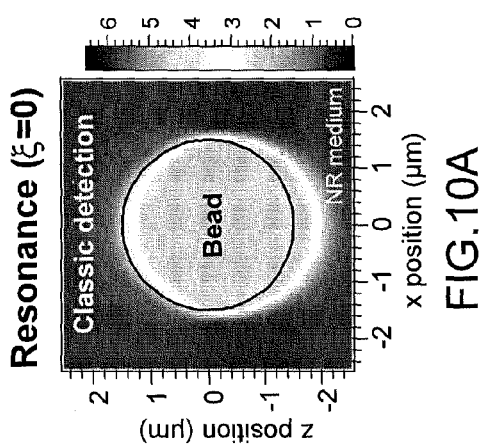
Figure 10D:
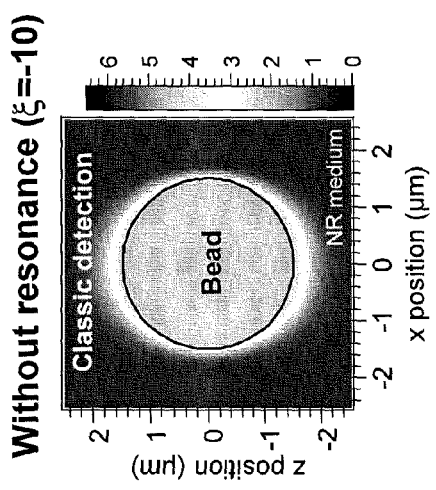

FIGS. 10A to 10D present numerical simulations obtained with the method according to the invention on another type of sample. The images are calculated by taking as a sample a bead of 3-μm diameter in an aqueous solvent (pump wavelength 730 nm, Stokes wavelength 814 nm, numerical aperture in water of the excitation lens 1.2, numerical aperture in water of the collecting lens 1.2). The image is calculated in each case in a plane XZ of the bead corresponding to a longitudinal plane comprising the direction of incidence of the excitation beams. FIGS. 10A and 10B represent an image of the bead in conventional detection, in other words only the CARS scattered signal in case α is represented. On-resonance (FIG. 10A), the signal is more intense than off-resonance (FIG. 10B), but the contrast difference is weak due to the non-resonant contributions of the bead and of its environment. FIGS. 10C and 10D represent images of the bead on-resonance and off-resonance, but calculated with the Dz-CARS method according to the invention, in other words by subtracting the CARS scattered signals in cases α and β, with a setup of the type of FIG. 8A. Off-resonance (FIG. 10D), the contrast is zero, because the difference in the signals which contain only a non-resonant contribution is cancelled out. In contrast, in FIG. 10C, calculated on-resonance, the contrast at the transverse interfaces is maximal. These results establish the feasibility of Dz-CARS in a microscopy configuration.

Figure 11:
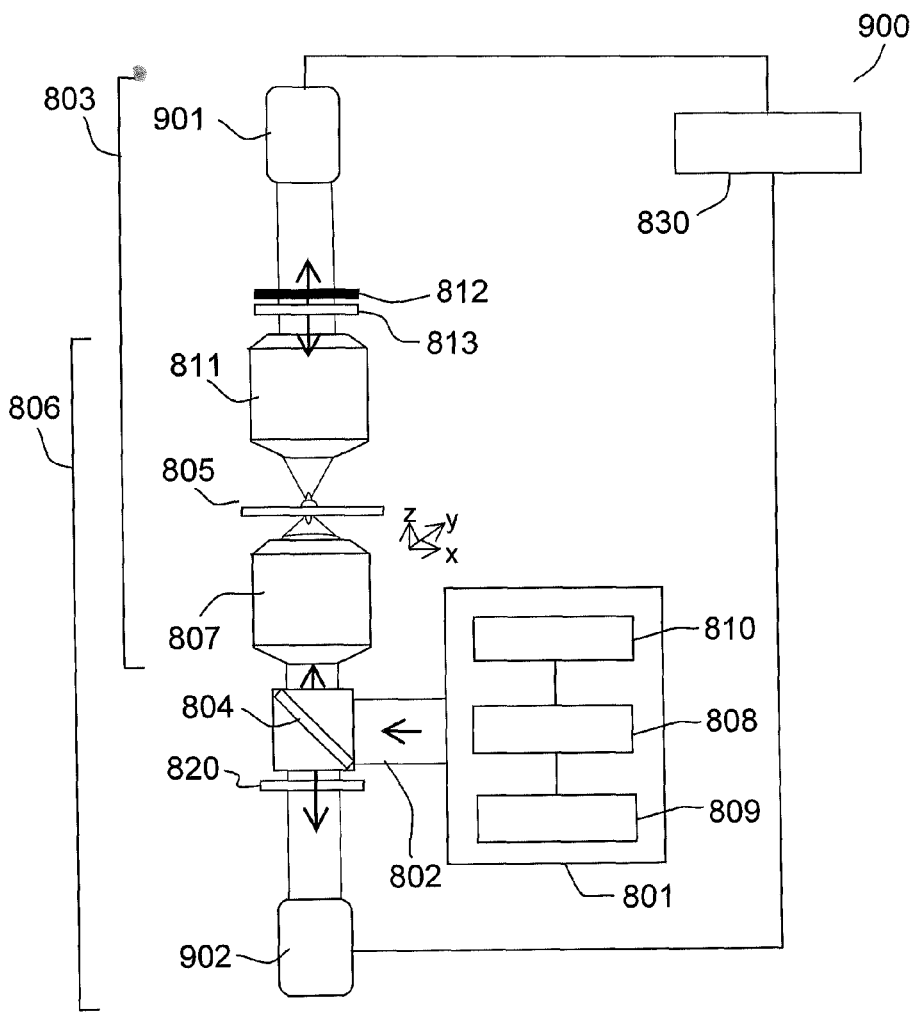
FIG. 11, example of the experimental setup for implementation of the method according to the invention according to a variant embodiment.

FIG. 11 illustrates an example experimental setup for implementation of the detection according to the invention according to a variant embodiment; The setup is substantially identical to that of FIG. 8A, but the point detectors 816, 817 are replaced by matrix detectors 901, 902, for example of CCD or CMOS type. According to this variant, the difference in CARS scattered signals integrated respectively for cases α and β in all the space of wave vectors $\vec{k}$ contained in the numerical aperture of detection lenses is no longer detected as previously; instead the difference in CARS scattered signals in symmetrical directions about the optical axis of the excitation beams incident on the sample is measured, the signals being detected for the first in case α, for the second in case β.

Figure 12A:
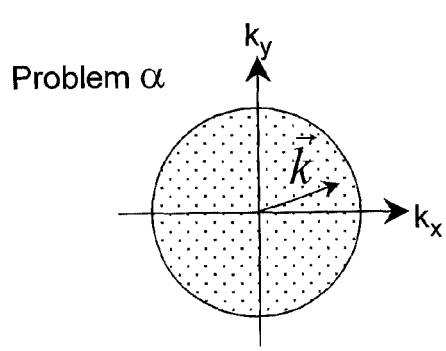
FIGS. 12A, 12B, illustrations of cases α and β for implementation of the method in the example of FIG. 11.
Figure 12B:
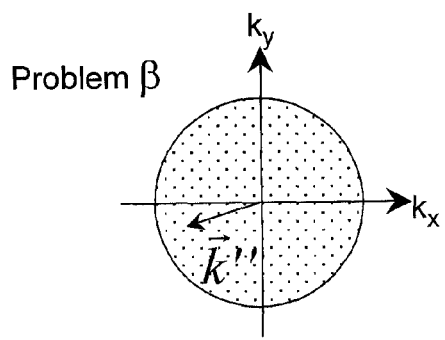

Thus, as is apparent in FIG. 12A, in case α, the CARS scattered signal is measured in a direction represented by the wave vector $\vec{k}$, of coordinates $k_x$, $k_y$ in the XY projection plane perpendicular to the main axis z, and in case β, the CARS scattered signal is measured in a direction represented by the wave vector $\vec{k}$ of coordinates $-k_x$, $-k_y$ in the XY projection plane. Here, as previously, case α corresponds to the generation of a CARS scattered signal resulting from the interaction of incident excitation beams with a sample, while case β corresponds to the generation of a CARS scattered signal resulting from the interaction of reflected excitation beams with the sample.

The Applicant has in fact demonstrated, both theoretically and experimentally, that besides allowing detection at the transverse interfaces of the sample, this method would allow detection at the axial interfaces of the sample, in other words having a non-zero component along the optical axis of the incident excitation beams. Hereinafter in the application, the method is called D-CARS.

Figure 13:
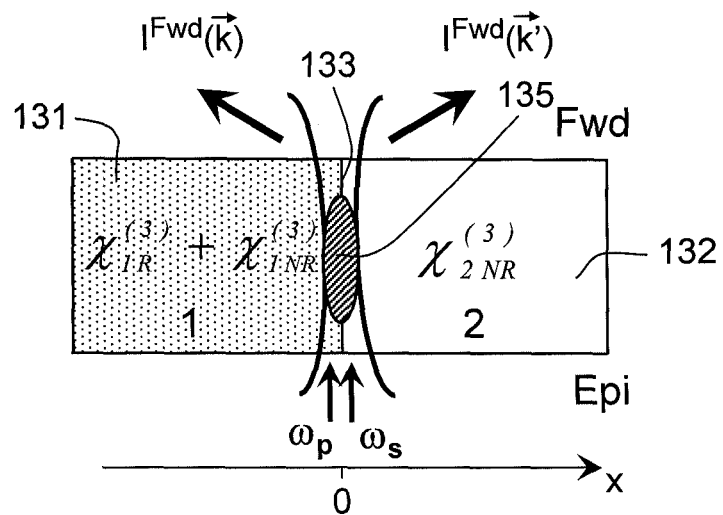
FIG. 13, diagram of the geometric conditions for implementing the CARS scattering at an axial interface between resonant and non-resonant media.
Figure 14:
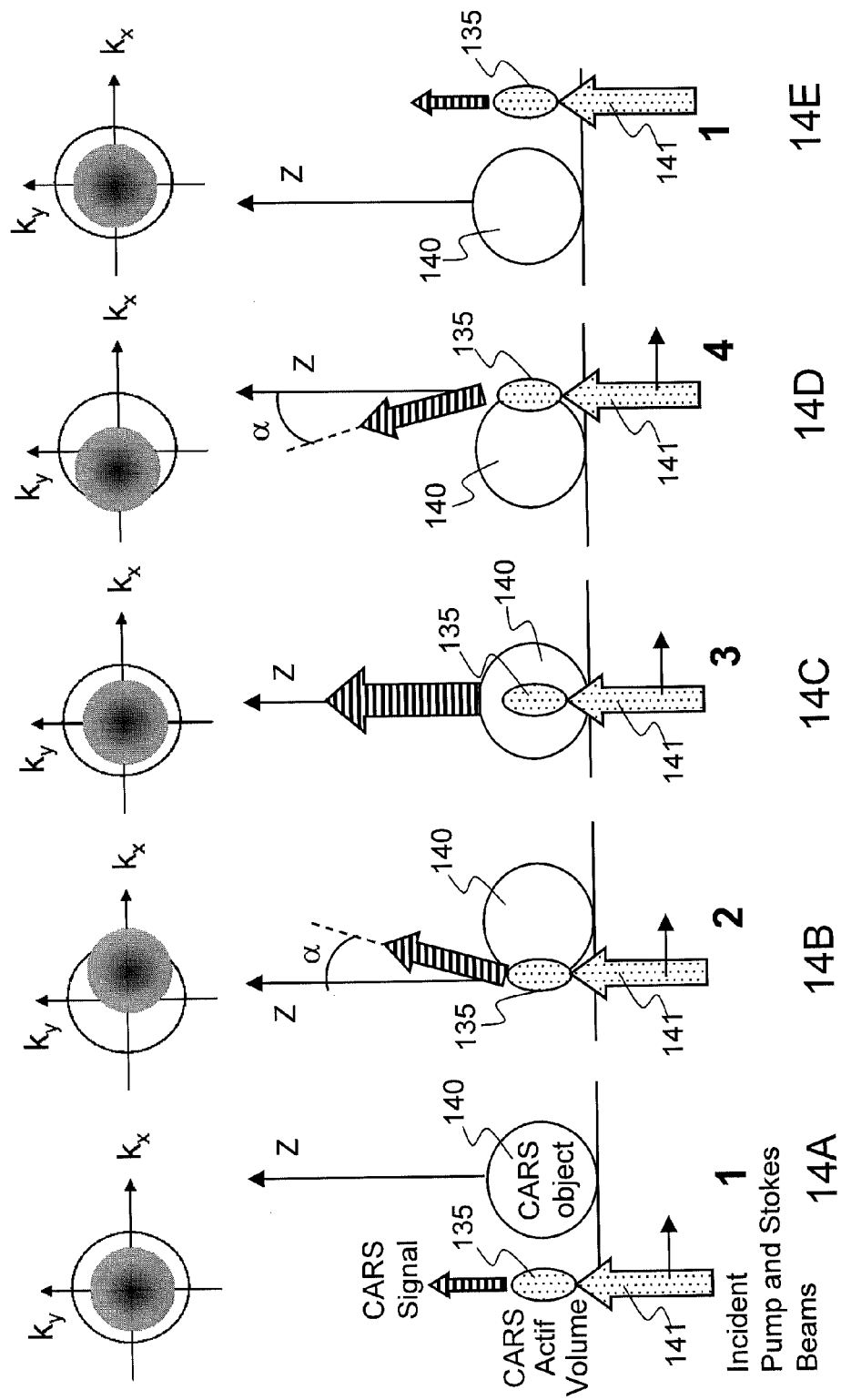
FIG. 14A to 14E, illustration of the deviation of the CARS scattered signal as a function of the relative position of the focal point of the excitation beams with an axial interface between resonant and non-resonant media.

For an improved understanding of D-CARS, FIGS. 13 to 15 illustrate, the following approach called Dk-CARS for detection at axial interfaces (Dk standing for Differential imaging in K-space).

FIG. 13 represents a sample comprising the resonant medium 131, for example a medium containing the medium to be analysed, in other words the medium of biological interest, and the non-resonant medium 132, typically a medium containing the solvent. The 3rd order nonlinear susceptibility is defined in the resonant medium 131 by a resonant term $\chi^{(3)}_{1R}$ and a non-resonant term $\chi^{(3)}_{1NR}$. In the non-resonant medium 132, it is defined by the non-resonant term $\chi^{(3)}_{2NR}$. According to this aspect of the method according to the invention, the pump excitation beam of angular frequency $\omega_p$ and probe excitation beam of angular frequency $\omega_s$, which are collinear, are incident on the sample in a focal volume 135, intercepting an axial interface 133 of the sample. According to this aspect of the method, as is explained in detail in what follows, analysis of the light intensity of the nonlinear optical beam in the space of wave vectors $\vec{k}$, that is, in the space of the emission directions of the signal emitted by the CARS process, on both sides of the interface, this intensity being indicated in FIG. 13 $I^{Fwd}(\vec{k})$ and $I^{Fwd}(\vec{k})$ on both sides of the interface respectively, the abbreviation "Fwd" representing the CARS forward scattered signal, as opposed to the signal called "Epi", scattered in a backward direction.

Indeed, the Applicant has demonstrated experimentally and theoretically that at an axial interface, the signal emitted by the CARS process is deviated at the resonance.

FIGS. 14A to 14E represent, by a series of diagrams, the deviation of the CARS scattered signal as a function of the relative position of the pump and Stokes beams incident with the interface. FIGS. 14A to 14E represent the active CARS volume 135 (focal point of the pump and Stokes beams) which is displaced through a CARS object 140 (each illustration corresponds to a different position of the active volume in the object). The CARS object is considered as resonant when the medium surrounding the object is considered as non-resonant (in the rest of the description it will be called "the solvent"). It appears that, at the interfaces between the CARS object and the solvent, the CARS scattered signal is affected by a deviation (or tilt). The Applicant has demonstrated that this deviation arises from a purely interferential process between the CARS object and the solvent and is in no way due to refractive effects. In the two illustrations 1 (FIGS. 14A and 14E), the CARS volume is focused in the solvent and the CARS scattered signal is emitted in the normal direction (parallel to the axis of incidence of the pump and Stokes beams, symbolised by the arrow 141); in illustration 2 (FIG. 14B), the CARS volume is focused on the interface between the CARS object and the solvent, the CARS scattered signal is then emitted at a positive angle α (relative to the axis of incidence of the pump and Stokes beams), thus deviating the beam in a direction defined by ($k_x$>0) in the space of wave vectors $\vec{k}$. In illustration 3 (FIG. 14C), the CARS volume is centred in the CARS object, the CARS signal is then intense and is directed in the normal direction (parallel to the axis of incidence of the pump and Stokes beams). A similar situation is then found in the following illustrations (illustration 4, FIG. 14D and illustration 1, FIG. 14E); however, it is important to note that in illustration 4, α is negative and corresponds to a deviation in a direction defined by ($k_x$<0). The Applicant has demonstrated both theoretically and experimentally that the change in angle α as a function of the normalised parameter $\zeta=(\omega_p-\omega_s-\Omega_R)\Gamma$ (where $\Gamma$ is the spectral width of the vibrational line studied), follows the phase of the tensor $\chi^{(3)}_1=\chi^{(3)}_{1R}+\chi^{(3)}_{1NR}$ describing medium 1. The Applicant has also demonstrated that by analysing the CARS signal in the symmetrical scattering directions, it is possible to determine the Raman spectrum.

Figure 15A:
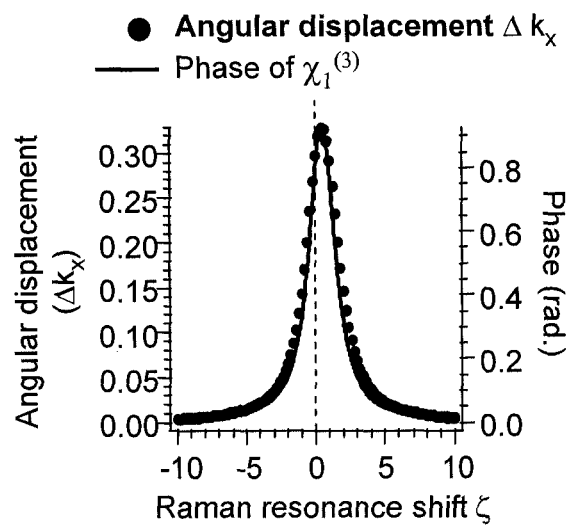
FIGS. 15A to 15C, curves obtained by numerical simulation, illustrating the shift in the CARS scattered signal as function of the parameter. $\zeta=(\omega_p-\omega_s-\Omega_R)/\Gamma$ (normalised Raman shift) (FIG. 15A), the light intensities calculated respectively in the space of ($k_x>0$) and ($k_x<0$) and the difference in intensities, as a function of the parameter $\zeta$ (FIG. 15B) and the x position of the focal point of the excitation beams relative to an axial interface (FIG. 15C)

FIG. 15A shows the results of a rigorous numerical calculation considering the vectorial nature of the pump and Stokes beams focused on an axial interface between a resonant medium 1 and a non-resonant medium 2 (FIG. 13). The analysis consists in studying in the space of wave vectors $\vec{k}$ the deviation of the CARS scattered signal emitted as a function of the normalised Raman shift $\zeta=(\omega_p-\omega_s-\Omega_R)/\Gamma$. Off-resonance ($\zeta$=−10), the beam is centred, while on-resonance ($\zeta$=0), an angular displacement clearly appears.

Figure 15B:
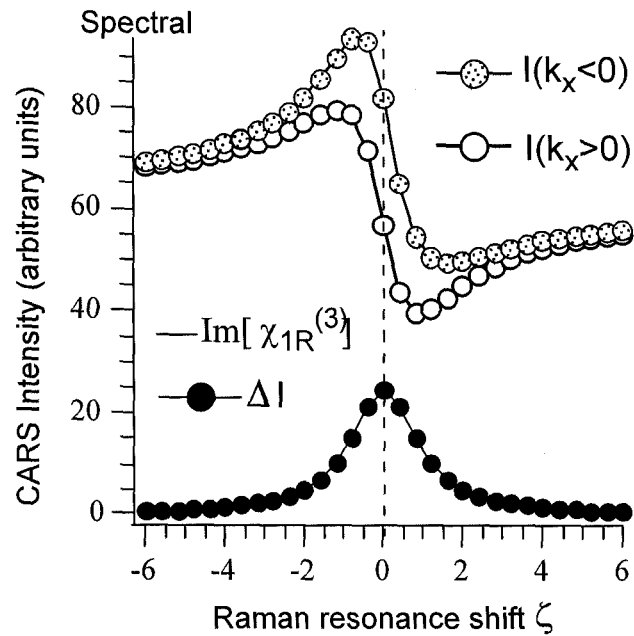
Figure 15C:
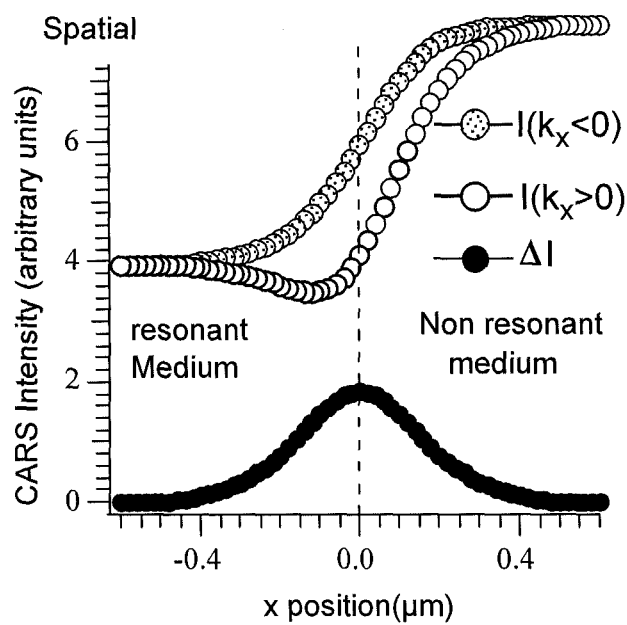

FIGS. 15B and 15C represent numerical simulations in which the CARS scattered signal is integrated into the half-spaces ($k_x$>0) and ($k_x$<0) respectively, then the difference in the signals thus integrated is determined. FIG. 15B shows the CARS spectra integrated on the half-spaces ($k_x$>0) and ($k_x$<0) when the pump and Stokes beams are focused on the interface (x=0), as well as their difference ΔI. This difference exactly follows the Raman spectrum given by Im[$\chi^{(3)}_{1R}$]. This demonstrates the pertinence of the Dk-CARS approach for a CARS spectroscopy without non-resonant noise. It is thus for example possible, by varying the frequency of the Stokes beam, to determine the Raman spectrum of the resonant medium. FIG. 15CB represents the CARS signals integrated on half-spaces ($k_x$>0) and ($k_x$<0) as a function of the focal point of the pump and Stokes beams relative to the interface. Their difference is non-zero uniquely in the vicinity of the interface (x=0). A non-resonant CARS image without background noise can thus be obtained in the vicinity of the interface.

Figures 16A, 16B, 16C:
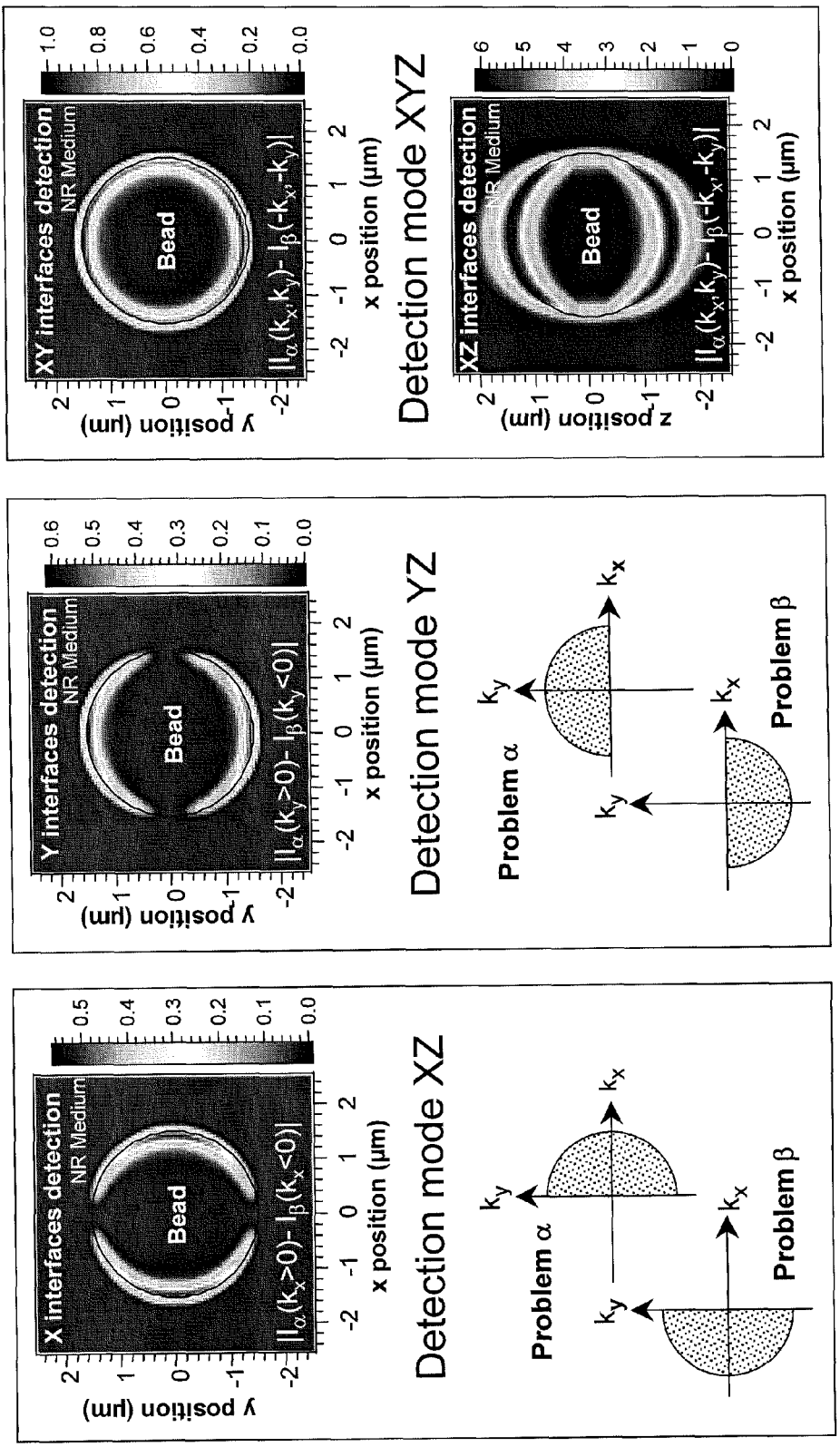
FIGS. 16A to 16C, diagrams illustrating 3 possible modalities for implementation of the CARS detection according to the invention.

FIGS. 16A to 16C thus present 3 possible detection modalities for the D-CARS microscopy combining the Dz-CARS and Dk-CARS approaches. For each detection modality, a numerical simulation represents the image obtained for a bead of 3-μm diameter in an aqueous solvent (pump wavelength 730 nm, Stokes wavelength 814 nm, numerical aperture in water of the excitation lens 1.2, numerical aperture in water of the collecting lens 1.2). FIG. 16A represents the XZ detection modality enabling detection at the interfaces perpendicular to the X axis and at the interfaces perpendicular to the Z axis. For this, the difference of the CARS scattered signals in cases α and β respectively is calculated by integrating the CARS signal in space ($k_x$>0) (case α, FIG. 7A) and in space ($k_x$<0) (case β, FIG. 7B), the referential system selected being that of the direction of the excitation beams. Thus, for example, by changing the relative position of the focal point of the pump and Stokes beams, the image of FIG. 16A is obtained in an equatorial plane of the bead. FIG. 16B represents the YZ detection modality allowing detection at the interfaces perpendicular to the Y axis and at the interfaces perpendicular to the Z axis. In this example, for different positions, the difference in light intensities integrated in space ($k_y$>0) (case α, FIG. 7A) and in space ($k_y$<0) (case β, FIG. 7B) is calculated. FIG. 16C shows detection modality XYZ. The image is calculated by taking the two by two difference in light intensities $I_\alpha(k_x, k_y)$ and $I_\beta(-k_x, -k_y)$ measured in two opposing directions $\vec{k}$ ($k_x, k_y, k_z$) and $\vec{k}'$ ($-k_x, -k_y, k_z$), in cases α and β respectively, the directions being contained in the angular cone, the aperture angle of which is defined by the numerical aperture for collection of the CARS scattered signal (for example 1.2 in water). Again, the coordinates of wave vectors $\vec{k}'$ and $\vec{k}''$ are expressed in the reference of the excitation beams specific to cases α and β respectively.

In the example of FIG. 11, it will advantageously be possible to provide means for angular scanning of the excitation beams, in particular for microscopy applications. As in the example of the device in FIG. 8A, it will be possible to select a spherical mirror 813 for reflecting the excitation beams 813. Furthermore, it is advantageous to position cameras 901, 902 in the exit pupils of lenses 811, 807 respectively, so as to keep the direction of incidence of the excitation beams centred on the camera in each of cases α and β. A calibration of cameras in solution is also possible to identify, in each case α and β, and for each scanning angle, the direction of the excitation beams relative to which the deviation of the CARS scattered signal will be measured.

Dz-CARS or D-CARS detection has been described by means of the implementation examples of FIGS. 8A and 11 in a bi-colour application, using two spectrally narrow laser sources. In the application called multiplex, a spectrally wide emission source of the Stokes beam can be chosen, generated, for example, by a femtosecond pulse or by a supercontinuum generated by an optical fibre or another dispersive medium. The pump signal remains spectrally narrow. In this application, it will be possible to acquire a Raman spectrum in a single pulse, for example, by using two slit spectrometers or a single spectrometer equipped with a CCD camera into which the two signals detected in the two cases α and β are injected. In this application, it is a matter of acquiring the spectrums in each of the cases (α or β) and making their difference.

In an application called a tricolour application, three wavelengths of associated frequencies $\omega_1$, $\omega_2$ and $\omega_3$ are used to generate a CARS signal at angular frequency $\omega_1-\omega_2+\omega_3$. The CARS signal may be rendered non-resonant without noise by detecting the signals at the angular frequency $\omega_1-\omega_2+\omega_3$ in the cases (α or β) and taking their difference.

Although the detection method has been described in the case of CARS scattering, it applies just as well to other nonlinear, 2nd or 3rd order processes, both for spectroscopy applications and for microscopy applications by detection at axial interfaces, thus enabling the interfaces between the resonant and non-resonant media to be revealed. In each case, an analysis of the nonlinear optical signal resulting from the interaction of one or more excitation beams is performed with a sample presenting an interface between a resonant medium and a non-resonant medium. This spatial analysis allows either the interface between the resonant medium and the non-resonant medium to be revealed, or a spectrum of the resonant medium to be characterised.

According to one example, a process for generating the third resonant harmonic can be used wherein the resonance is an electronic resonance, by exciting a sample comprising an interface between a resonant medium and a non-resonant medium with a single pump excitation beam, of angular frequency $\omega_p$. For example a picosecond or femtosecond laser source of the oscillator type Ti: Sapphire, Nd: glass, or ytterbium or erbium-doped optical fibres.

According to another example, a four-wave mixing process can be used wherein the resonance is an electronic resonance, by exciting a sample comprising an interface between a resonant medium and a non-resonant medium with a single pump excitation beam, of angular frequency $\omega_p$. For example a picosecond or femtosecond laser source of the oscillator type Ti: Sapphire, Nd: glass, or ytterbium or erbium-doped optical fibres.

The two examples described above deal with electronic resonances. They are found in atoms, molecules, semi-conductor crystals, etc.

According to another embodiment, the second resonant harmonic can be excited with a single pump beam, or the sum of the frequency can be made with a pump beam and probe beam (nonlinear effect of the 2nd order).

Although described using a certain number of detailed example embodiments, the detection device and method according to the invention comprise different variants, modifications and developments which will be obvious to the person skilled in the art, it being understood that these different variants, modifications and developments fall within the scope of the invention, as defined by the claims below.

The invention claimed is:

1. A device for detecting a resonant nonlinear optical signal induced in a sample of a type comprising a resonant medium and a non-resonant medium forming an interface, the device comprising:
    an emission source of at least one first excitation light beam, called a pump beam, at a first given angular frequency $\omega_p$, for the excitation of a resonant medium of a sample of the given type;
    a first optical module for detecting a first nonlinear optical forward CARS signal resulting from a first interaction of said pump beam with the sample when said pump beam is incident on the sample along an optical axis and intercepts the sample at a given position of a transverse interface between the resonant medium and the non-resonant medium of the sample;
    means of reflection of said pump beam, arranged in such a way that said reflected pump beam intercepts said transverse interface substantially at the same position as said incident pump beam;
    a second optical module, separate from the first optical module, for detecting a second nonlinear optical forward CARS signal resulting from a second interaction of said reflected pump beam with the sample;
    a processing module for processing optical signals detected by said first and second detection modules, comprising the calculation of a difference in detected signals, the difference being characteristic of a vibrational or electronic resonance of the resonant medium.

2. The device according to claim 1, wherein
    the emission source allows the emission of at least a second excitation beam for the excitation of the resonant medium, at at least a second angular frequency $\omega_s$, different from the first angular frequency $\omega_p$, all of the excitation beams being collinear, arranged so as to intercept said transverse interface at said position in a common focal volume,
    the means of reflection are arranged in such a way as to reflect all the excitation beams on said transverse interface, at the same position on the interface, the difference in the signals detected by the first and second detection module is characteristic of a vibrational or electronic resonance of the resonant medium at an angular frequency equal to a linear combination of frequencies of the first and second frequencies.

3. The device according to claim 2, wherein the emission source allows the emission of a pump beam of angular frequency $\omega_p$ and a Stokes beam of angular frequency $\omega_s$, the first and the second nonlinear optical forward CARS signals resulting from the first and the second interaction of said pump and Stokes beams being a signal of angular frequency $\omega_{as}=2\omega_p-\omega_s$ and the difference in signals detected by the first and second detection module being characteristic of a Raman resonance of the resonant medium.

4. The device according to claim 1, wherein the means of reflection are formed by a reflecting mirror allowing the excitation beam or beams to be reflected and to transmit said first nonlinear optical forward CARS signal.

5. The device according to claim 4, wherein the reflecting mirror is spherical.

6. The device according to claim 1, further comprising:
a focusing lens for focusing said incident excitation beam or beams in a common focal volume, allowing said interface between the resonant medium and the non-resonant medium to be intercepted; and
a collecting lens for collecting the first nonlinear optical forward CARS signal resulting from the first interaction of the incident excitation beams with the sample, said collecting lens being identical to the focusing lens of the incident beams,
said collecting lens forming a focusing lens for focusing the reflected excitation beams and said focusing lens for focusing incident beams forming a collecting lens for collecting the second nonlinear optical forward CARS signal resulting from the second interaction of the reflected excitation beams with the sample.

7. The device according to claim 1, further comprising a dichroic beamsplitter allowing the excitation beam or beams emitted by the emission source to be directed towards the sample and allowing the second nonlinear optical forward CARS signal resulting from the second interaction of the reflected excitation beam with the sample to pass.

8. The device according to claim 1, wherein each of the optical detection modules comprises an image recording device, the first and the second nonlinear optical forward CARS signals being collected in the first and the second optical detection modules respectively in symmetrical directions about the optical axis, the difference being effected for each signal couple thus detected.

9. The device according to claim 1, further comprising a device providing an angular scan of the excitation beam or beams, allowing the excitation beam or beams to intercept the sample at different positions of the interface between the resonant and non-resonant medium.

10. The device according to claim 1, wherein the emission source emits at least one variable wavelength excitation beam, allowing a spectrum of vibrational or electronic resonances of the resonant medium to be obtained.

11. A method for detecting a resonant non-linear optical signal induced in a sample, the sample comprising a resonant medium and a non-resonant medium forming an interface, the method comprising:
the emission of at least one first excitation light beam of the resonant medium, called a pump beam, at a first given angular frequency $\omega_p$, said pump beam being incident on the sample along an optical axis, and intercepting the sample at a given position of a transverse interface between the resonant and non-resonant medium;
the detection, by a first optical module, of a first nonlinear optical forward CARS signal resulting from a first interaction of said excitation beam or beams with the sample;
the reflection of said excitation beam or beams, the excitation beam or beams thus reflected intercepting said transverse interface substantially at the same position as the incident excitation beam or beams;
the detection, by a second optical module, of a second nonlinear optical forward CARS signal resulting from a second interaction of said reflected excitation beam or beams with the sample; and
the processing of the first and second detected optical signals, comprising the calculation of a difference between the detected signals, the difference being characteristic of a vibrational or electronic resonance of the resonant medium.

12. The method according to claim 11, further comprising:
the emission of at least one second excitation beam of the resonant medium, at at least a second angular frequency $\omega s$ different from the first angular frequency $\omega p$, all of the excitation beams being collinear, and intercepting said transverse interface at said position in a common focal volume; and
the difference in the first and second detected signals being characteristic of a vibrational or electronic resonance of the resonant medium at an angular frequency equal to a linear combination of the frequencies of the first and second frequencies.

13. The method according to claim 12, comprising the emission of a pump beam of angular frequency op and a Stokes beam of angular frequency $\omega_s$, the the first and the second nonlinear optical forward CARS signals resulting from the first and the second interactions of said pump and Stokes beams being, of angular frequency $\omega_{as}=2\omega_p-\omega_s$ and the difference in the first and second detected signals being characteristic of a Raman resonance of the resonant medium.

14. The method according to claim 11, wherein said first and second nonlinear optical forward CARS signals are detected respectively in directions symmetrical about the optical axis of the incident excitation beams, the difference being effected for each signal couple thus detected.

15. The method according to claim 11, wherein the excitation beam or beams are subject to an angular scan to intercept the sample at various positions of the interface between the resonant and non-resonant medium.

16. The method according to claim 11, wherein at least one of the excitation beams has a variable emission wavelength, allowing a spectrum of vibrational or electronic resonances of the resonant medium to be obtained.

* * * * *